United States Patent
Fukuda et al.

(10) Patent No.: US 7,727,762 B2
(45) Date of Patent: Jun. 1, 2010

(54) METHOD OF INDUCING THE DIFFERENTIATION OF STEM CELLS INTO MYOCARDIAL CELLS

(75) Inventors: Keiichi Fukuda, Tokyo (JP); Shinsuke Yuasa, Tokyo (JP); Hideyuki Okano, Tokyo (JP); Takuya Shimazaki, Tokyo (JP); Uichi Koshimizu, Osaka (JP); Tomofumi Tanaka, Ibaraki (JP); Keijiro Sugimura, Ibaraki (JP)

(73) Assignee: Keiichi Fukuda, Tokyo (JP)

( * ) Notice: Subject to any disclaimer, the term of this patent is extended or adjusted under 35 U.S.C. 154(b) by 635 days.

(21) Appl. No.: 10/574,530

(22) PCT Filed: Oct. 4, 2004

(86) PCT No.: PCT/JP2004/014598

§ 371 (c)(1),
(2), (4) Date: Jul. 21, 2006

(87) PCT Pub. No.: WO2005/033298

PCT Pub. Date: Apr. 14, 2005

(65) Prior Publication Data

US 2007/0134215 A1    Jun. 14, 2007

(30) Foreign Application Priority Data

Oct. 3, 2003   (JP)   ............................. 2003-346248
Jul. 20, 2004   (JP)   ............................. 2004-212255

(51) Int. Cl.
*C12N 5/00* (2006.01)
*C12N 5/02* (2006.01)
*C12N 15/74* (2006.01)
*C12N 5/071* (2010.01)
*C12N 5/07* (2010.01)
*C12N 5/10* (2006.01)

(52) U.S. Cl. ................ 435/377; 435/475; 435/366; 435/363

(58) Field of Classification Search .............. 435/377, 435/475, 366, 363
See application file for complete search history.

(56) References Cited

OTHER PUBLICATIONS

Bin, Z et al, 2006, Efficient cardiomyocyte differentiation of embryonic stem cells by bone morphogenetic protein-2 combined with visceral endoderm-like cells, Cell Biology International, 30:769-776.*
Rajasingh, J et al, 2007, STAT-3-dependent mouse embryonic stem cell differentiation into cardiomyocytes, Circ. Res. 101:910-918.*
Ruhnke et al, 2003, Stem Cells, 24:428-436.*
Keller, GM, 2005, Genes and Development, 19:1129-1155.*
Wang, G et al, 2005, Noggin and bFGF cooperate to maintain pluripotency of human embryoic stem cells in the absence of feeder layers, BBRC, 330:934-942.*
Zhang et al, 2001, Am J Physiol Heart Circ Physiol, 280:H1782-1792.*
Monzen et al., "Bone Morphogenetic Proteins Induce Cardiomyocyte Differentiation through the Mitogen-Activated Protein Kinase Kinase Kinase TAK1 and Cardiac Transcription Factors Csx/Nkx-2.5 and GATA-4." Molecular and Cellular Biology, vol. 19, No. 10, pp. 7096-7105, Oct. 1999.
Kawai, et al. "Efficient Cardiomyogenic Differentiation of Embryonic Stem Cell by Fibroblast Growth Factor 2 and Bone Morphogenetic Protein 2." Circulation Journal, vol. 68, pp. 691-702, Jul. 2004.
Pera, et al., "Regulation of Human Embryonic Stem Cell Differentiation by BMP-2 and its Antagonist Noggin", Journal of Cell Science, vol. 117, p. 1269-1280, 2004.
Yuasa, et al., "Transient Inhibition of BMP Signaling by Noggin Induces Cardiomyocyte Differentation of Mouse Embryonic Stem Cells", Nature Biotechnology, vol. 23, No. 5, p. 607-611, May 2005.
Monzen, et al. (May 14, 2001) "Smads, TAK1, and their Common Target ATF-2 Play a Critical Role in Cardiomyocyte Differentiation." The Journal of Cell Biology 153(4): 687-698.

* cited by examiner

*Primary Examiner*—Valarie Bertoglio
(74) *Attorney, Agent, or Firm*—Hunton & Williams LLP

(57) ABSTRACT

For a method of inducing differentiation of cardiomyocytes from stem cells, a method is provided to induce efficiently and selectively differentiation of cardiomyocytes by such a method in which the stem cells are cultured to induce differentiation into cardiomyocytes in the presence of a substance that inhibits BMP signaling.

17 Claims, 10 Drawing Sheets

SEQUENCE LISTING

<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: forward primer for amplifying GATA-4

```
<400> SEQUENCE: 1
ctgtcatctc actatgggca                                              20

<210> SEQ ID NO 2
<211> LENGTH: 20
<212> TYPE: DNA
<213> ORGANISM: Artificial
<220> FEATURE:
<223> OTHER INFORMATION: reverse primer for amplifying GATA-4

<400> SEQUENCE: 2
ccaagtccga gcaggaattt                                              20

<210> SEQ ID NO 3
<211> LENGTH: 20
<212> TYPE: DNA
<213> ORGANISM: Artificial
<220> FEATURE:
<223> OTHER INFORMATION: forward primer for amplifying TEF-1

<400> SEQUENCE: 3
aagacgtcaa gccctttgtg                                              20

<210> SEQ ID NO 4
<211> LENGTH: 20
<212> TYPE: DNA
<213> ORGANISM: Artificial
<220> FEATURE:
<223> OTHER INFORMATION: reverse primer for amplifying TEF-1

<400> SEQUENCE: 4
aaaggagcac actttggtgg                                              20

<210> SEQ ID NO 5
<211> LENGTH: 20
<212> TYPE: DNA
<213> ORGANISM: Artificial
<220> FEATURE:
<223> OTHER INFORMATION: forward primer for amplifying Tbx-5

<400> SEQUENCE: 5
ggagcctgat tccaaagaca                                              20

<210> SEQ ID NO 6
<211> LENGTH: 20
<212> TYPE: DNA
<213> ORGANISM: Artificial
<220> FEATURE:
<223> OTHER INFORMATION: reverse primer for amplifying Tbx-5

<400> SEQUENCE: 6
ttcagccaca gttcacgttc                                              20

<210> SEQ ID NO 7
<211> LENGTH: 20
<212> TYPE: DNA
<213> ORGANISM: Artificial
<220> FEATURE:
<223> OTHER INFORMATION: forward primer for amplifying MEF-2c

<400> SEQUENCE: 7
agcaagaata cgatgccatc                                              20

<210> SEQ ID NO 8
<211> LENGTH: 20
```

```
<212> TYPE: DNA
<213> ORGANISM: Artificial
<220> FEATURE:
<223> OTHER INFORMATION: reverse primer for amplifying MEF-2c

<400> SEQUENCE: 8 gaagggtgg tggtacggtc                                              20

<210> SEQ ID NO 9
<211> LENGTH: 23
<212> TYPE: DNA
<213> ORGANISM: Artificial
<220> FEATURE:
<223> OTHER INFORMATION: forward primer for amplifying alphaMHC

<400> SEQUENCE: 9
ggaagagtga gcggccatca agg                                         23

<210> SEQ ID NO 10
<211> LENGTH: 22
<212> TYPE: DNA
<213> ORGANISM: Artificial
<220> FEATURE:
<223> OTHER INFORMATION: reverse primer for amplifying alphaMHC

<400> SEQUENCE: 10
ctgctggaga ggttattcct cg                                          22

<210> SEQ ID NO 11
<211> LENGTH: 20
<212> TYPE: DNA
<213> ORGANISM: Artificial
<220> FEATURE:
<223> OTHER INFORMATION: forward primer for amplifying MLC-2v

<400> SEQUENCE: 11
gccaagaagc ggatagaagg                                             20

<210> SEQ ID NO 12
<211> LENGTH: 20
<212> TYPE: DNA
<213> ORGANISM: Artificial
<220> FEATURE:
<223> OTHER INFORMATION: reverse primer for amplifying MLC-2v

<400> SEQUENCE: 12
ctgtggttca gggctcagtc                                             20

<210> SEQ ID NO 13
<211> LENGTH: 24
<212> TYPE: DNA
<213> ORGANISM: Artificial
<220> FEATURE:
<223> OTHER INFORMATION: forward primer for amplifying alpha-cardiac
      actin

<400> SEQUENCE: 13
ctgagatgtc tctctctctc ttag                                        24

<210> SEQ ID NO 14
<211> LENGTH: 20
<212> TYPE: DNA
<213> ORGANISM: Artificial
<220> FEATURE:
<223> OTHER INFORMATION: reverse primer for amplifying alpha-cardiac
      actin
```

-continued

```
<400> SEQUENCE: 14
acaatgactg atgagagatg                                          20

<210> SEQ ID NO 15
<211> LENGTH: 19
<212> TYPE: DNA
<213> ORGANISM: Artificial
<220> FEATURE:
<223> OTHER INFORMATION: forward primer for amplifying GAPDH

<400> SEQUENCE: 15
ttcaacggca cagtcaagg                                           19

<210> SEQ ID NO 16
<211> LENGTH: 19
<212> TYPE: DNA
<213> ORGANISM: Artificial
<220> FEATURE:
<223> OTHER INFORMATION: reverse primer for amplifying GAPDH

<400> SEQUENCE: 16
catggactgt ggtcatgag                                           19
```

METHOD OF INDUCING THE DIFFERENTIATION OF STEM CELLS INTO MYOCARDIAL CELLS

CROSS-REFERENCE TO RELATED APPLICATIONS

This application is a U.S. national stage application of International Application No. PCT/JP2004/014598, filed on Oct. 4, 2004, which claims the benefit of Japanese Patent Application No. 2003-346248, filed on Oct. 3, 2003 and Japanese Patent Application No. 2004-212255, filed Jul. 20, 2004, the disclosures of each of which are herein incorporated by reference in their entireties.

BACKGROUND OF THE INVENTION (i) Field of the Invention

The present invention relates to a method of preparing cardiomyocytes selectively and efficiently from ES cells and other pluripotent stem cells, and to cells for regenerative medicine obtained by this method.

(ii) Description of the Related Art

In general, cardiomyocytes undergo active cell division with beating autonomously before birth, but immediately after birth they lose the ability to divide, and since they have little undifferentiated precursor cells, when cardiomyocytes die due to exposure to various forms of stress including myocardial infarction, myocarditis and the like, the lost cardiomyocytes cannot be replaced. As a result, the surviving cardiomyocytes try to maintain myocardial function through compensatory hypertrophy and the like, but if the stress continues and exceeds an allowable threshold, it leads to further exhaustion and death of cardiomyocytes and a consequent lowering of myocardial function (that is, heart failure).

Heart failure and other types of heart disease are the second leading cause of death in Japan, and prognoses are very poor, with a 5-year survival rate of only about 50% for patients with heart diseases. Therefore, it is hoped that development of highly effective therapies for heart failure will lead to great advances in medical welfare as well as improved medical economics. Conventional therapeutic drugs for heart failure include digitalis preparations that increase the contractive force of the myocardium and xanthine preparations and other heart stimulants, but long-term administration of these drugs is known to make the condition worse because there is too much expenditure of myocardial energy. More recently, mainstream therapy has shifted to beta-blockers and ACE inhibitors, which reduce the excess burden on the heart due to stimulation of the sympathetic nervous system and rennin-angiotensin system, but these methods only deal with the immediate symptoms and cannot restore damaged cardiac tissue. By contrast, heart transplantation is a fundamental treatment for severe heart failure, but it is one that is difficult to apply commonly because of such problems as the shortage of heart donors, ethical concerns, the physical and financial burden on patients and the like.

Therefore, it would seem that methods of transplantation to replace weakened or lost cardiomyocytes would be extremely useful for the treatment of heart failure. In fact, it is known from animal experiments that when immature cardiomyocytes obtained from fetuses are transplanted into adult cardiac tissue, the transplanted cells function effectively (See Non-Patent Document 1). However, it is difficult to obtain sufficient cardiomyocytes for this method, and application to clinical medicine is also difficult from an ethical standpoint.

Attention has therefore focused in recent years on inducing differentiation of stem cells into cardiomyocytes and using these cells for transplantation. At present it has not yet been possible to clearly identify a population of precursor cells or stem cells capable of producing cardiomyocytes in adult cardiac tissue, so pluripotent stem cells, which are less differentiated and can differentiate into a variety of cells, are considered to be useful for above method.

Pluripotent stem cells are defined as cells which are capable of indefinite or long-term cell proliferation while remaining in an undifferentiated state in an in vitro culture, which retain normal karyotypes, and which have the ability to differentiate into all of three germ layers (ectoderm, mesoderm and endoderm). At present, the three well-known pluripotent stem cells are embryonic stem cells (ES cells) derived from early-stage embryos, embryonic germ cells (EG cells) derived from primordial germ cells at the embryonic stage, and multipotent adult progenitor cells (MAPC) isolated from adult bone marrow.

It has long been known that ES cells in particular can be induced to differentiate into cardiomyocytes in vitro. Most of the early studies were done by using ES cells derived from mice. When ES cells are cultured in floating culture as single cells (individual cells dispersed with no adhesion between cells due to enzyme treatment or the like) without the presence of a differentiation-inhibiting factor such as leukemia inhibitory factor (LIF) or the like, the ES cells adhere to one another and aggregate, forming a structure called embryoid bodies (EBs) which are similar to the early embryonal structures. It is also known that cardiomyocytes with spontaneous beating ability appear when these EBs are cultured in suspension or in adhesion on the surface of culture devices.

ES cell-derived cardiomyocytes prepared as described above exhibit very similar properties to those of immature cardiomyocytes in fetal hearts (See Non-Patent Documents 2 and 3). Moreover, it has been confirmed from animal experiments that when ES cell-derived cardiomyocytes are transplanted into adult cardiac tissues they are highly effective, with results similar to those obtained by transplantation of fetal myocardium (See Patent Document 1; Non-Patent Document 4).

In 1995, Thomson et al first established ES cells from primates (See Patent Document 2; Non-Patent Document 5), and thus the regeneration therapy using pluripotent stem cells-derived cardiomyocytes has become realistic. Subsequently they also succeeded in isolating and establishing human ES cell lines from early human embryos (See Non-Patent Document 6). Moreover, Gearhart et al established human EG cell lines from primordial human germ cells (See Non-Patent Document 7; Patent Document 3). Kehat et al (See Non-Patent Document 8) and Xu et al (See Patent Document 4; Non-Patent Document 9) have reported that human ES cells can differentiate into cardiomyocytes in vitro, as mouse ES cells can do. According to these reports, human ES cells-derived cardiomyocytes which have been induced to differentiate from human ES cells not only have the ability to beat spontaneously but also express and produce myocardial-specific proteins such as myosin heavy and light chains, alpha-actinin, troponin I and atrial natriuretic peptide (ANP) and myocardial-specific transcription factors such as GATA-4, Nkx2.5, MEF-2c and the like, and from microanatomical observation and electrophysiological analysis it appears that they retain the properties of immature cardiomyocytes at the fetal stage, and could be used for regenerative therapy.

However, one serious problem remains to be elucidated to use pluripotent stem cells-derived cardiomyocytes for cell transplantation therapy and other purposes. When EBs are formed from ES cells or EG cells by conventional methods, not only cardiomyocytes, but also other types of differentiated cells, such as blood cells, vascular cells, neural cells, intestinal cells, bone and cartilage cells and the like, are developed. Moreover, the proportion of cardiomyocytes in these differentiated cell population is not so high, only about 5 to 20% of the total.

Methods of isolating only cardiomyocytes from a mixture of various kinds of cells include a method of adding an artificial modification to the ES cell genes, conferring drug resistance or ectopic expression, and collecting cells having the properties of cardiomyocytes or precursor cells thereof. For example, by introducing a gene cassette capable of expressing a neomycin (G418) resistance gene under the control of the α-myosin heavy chain promoter into mouse ES cells, Field and his co-researchers established a system in which those ES cells, could only survive in medium to which G418 had been added when they differentiated into cardiomyocytes and expressed the α-myosin heavy chain gene (See Patent Document 1; Non-Patent Document 4). 99% or more of G418-resistant cells selected by this method were confirmed to be cardiomyocytes. However, although the purity of the cardiomyocytes is extremely high in this method the final number of cardiomyocytes obtained is only a few percent of the total cell count, making it difficult to obtain enough amounts of cardiomyocytes for transplantation.

Recently, Chunhui et al have reported that when human ES cells are treated with 5-azacytidine, the percentage of troponin I-positive cells (candidate cardiomyocytes) in EBs rises from 15% to 44% (See Non-Patent Document 9), but even in this method the percentage of cardiomyocytes in EBs does not exceed 50%. Moreover, 5-azacytidine is a demethylation agent that alters the expression of genes by removing methyl groups bound to DNA, and because it acts directly on the chromosomes, it is not a suitable drug for preparing cells for cell transplantation.

Other methods for producing cardiomyocytes more efficiently from ES cells include, in the case of mouse ES cells, addition of retinoic acid (See Non-Patent Document 10), ascorbic acid (See Non-Patent Document 11), TGF beta, BMP-2 (See Non-Patent Document 12), PDGF (See Non-Patent Document 13) and Dynorphin B (See Non-Patent Document 14) and treatment to increase reactive oxygen species (ROS) (See Non-Patent Document 15) and $Ca^{2+}$ (See Non-Patent Document 16) in the cells, all of which are known to act positively to induce cardiomyocyte differentiation. However, cardiomyocyte-specific, selective differentiation has not been achieved with any of these methods.

The secretory proteins Noggin and Chordin were initially identified as nerve induction factors in Xenopus embryos (See Non-Patent Documents 17 and 18; Patent Documents 5-8). Further study has shown that Noggin and Chordin bind with BMP (Bone Morphogenic Protein) family of molecules, which impair the signal transduction, and cause neural induction and differentiation. (See Non-Patent Documents 19-21). In fact, experiments using mouse ES cells have shown that nerve cell differentiation is induced in cells in which the Noggin or Chordin gene is constantly expressed (See Non-Patent Document 22).

When human ES cells are cultured in medium to which Noggin has been added, the function of endogenously produced BMP-2 is diminished, and ES cells into extraembryonic endodermal cells are impaired and so that they are maintained in an undifferentiated state. In addition, when noggin-treated ES cells are subsequently cultured under neural differentiation condition, the development of neural cells is induced (See Patent Document 9).

It has also been reported from earlier studies using chicken (See Non-Patent Document 23), Xenopus (See Non-Patent Document 24) and mouse embryonic carcinoma cells (See Non-Patent Document 25) that the BMP family of molecules acts to promote development and/or differentiation of cardiomyocytes, and when that action is blocked by Noggin treatment, development and/or differentiation of cardiomyocytes is suppressed.

Heretofore there have been no efforts to encourage development and differentiation of cardiomyocytes by using Noggin, Chordin or other BMP signal-inhibiting factors.

Patent Document 1: U.S. Pat. No. 6,015,671;
Patent Document 2: U.S. Pat. No. 5,843,780;
Patent Document 3: U.S. Pat. No. 6,090,622;
Patent Document 4: International Patent Disclosure 03/06950, pamphlet;
Patent Document 5: International Patent Disclosure 94/05791, pamphlet;
Patent Document 6: U.S. Pat. No. 5,679,783;
Patent Document 7: U.S. Pat. No. 5,846,770;
Patent Document 8: U.S. Pat. No. 5,986,056;
Patent Document 9: International Patent Disclosure 01/98463, pamphlet;
Non-Patent Document 1: Soonpaa et al, Science 264:98, 1994;
Non-Patent Document 2: Maltsev et al, Mech. Dev. 44:41, 1993;
Non-Patent Document 3: Maltsev et al, Circ. Res. 75: 233, 1994
Non-Patent Document 4: Klug et al, J. Clin. Invest. 98: 216, 1996;
Non-Patent Document 5: Thomson et al, Proc. Natl. Acad. Sci. USA 92:7844, 1995;
Non-Patent Document 6: Thomson et al, Science 282: 114, 1998;
Non-Patent Document 7: Shamblott et al, Proc. Natl. Acad. Sci. USA 95: 13726, 1998;
Non-Patent Document 8: Kehat et al, J. Clin. Invest. 108: 407, 2001;
Non-Patent Document 9: Xu et al. Circ. Res. 91: 501, 2002;
Non-Patent Document 10: Wobus et al, J. Mol. Cell. Cardiol. 29: 1525, 1997;
Non-Patent Document 11: Takahashi et al, Circulation 107: 1912, 2003;
Non-Patent Document 12: Behfar et. al, FASEB J. 16: 1558, 2002;
Non-Patent Document 13: Sachinidis et al, Cardiovasc. Res. 58: 278, 2003;
Non-Patent Document 14: Ventura et al, Circ. Res. 92: 623, 2003;
Non-Patent Document 15: Sauer et al, FEBS Lett. 476:218, 2000;
Non-Patent Document 16: Li et al, J. Cell Biol. 158: 103, 2002;
Non-Patent Document 17: Smith & Harland, Cell 70: 829, 1992;
Non-Patent Document 18: Sasai et al, Cell 79: 779, 1994;
Non-Patent Document 19: Re'em-Kalma et al, Proc. Natl. Acad. Sci. USA 92: 12141, 1995;
Non-Patent Document 20: Zimmerman et al, Cell 86: 599, 1996;
Non-Patent Document 21: Piccolo et al, Cell 86: 589, 1996;
Non-Patent Document 22: Gratsch & O'Shea, Dev. Biol. 245: 83, 2002;
Non-Patent Document 23: Schultheiss et al, Genes Dev., 11: 451, 1997;

Non-Patent Document 24: Sparrow et al, Mech. Dev. 71:151, 1998

Non-Patent Document 25: Monzen et al, Mol. Cell. Biol. 19:7096, 1999.

SUMMARY AND OBJECTS OF THE INVENTION

It is an object of the present invention to provide a method of inducing differentiation of stem cells into cardiomyocytes efficiently and selectively, along with cardiomyocytes obtained by this method and a method of using these cells in cell transplantation and injection and other therapies targeting heart disease.

DETAILED DESCRIPTION OF PREFERRED EMBODIMENTS

The present invention relates mainly to the following.

(1) A method for inducing cardiomyocyte differentiation of stem cells, wherein stem cells are cultured to induce differentiation in the presence of a substance that inhibits BMP signaling.

(2) The method according to (1) above, wherein culture of the stem cells to induce differentiation comprises a step of forming embryoid bodies by floating aggregation culture.

(3) The method according to (1) above, wherein culture of the stem cells to induce differentiation comprises a step of co-culturing with feeder cells.

(4) The method according to (1) above, wherein culture of the stem cells to induce differentiation comprises a step of plate culturing on a culture container.

(5) A method according to any one of (1) through (4) above, wherein comprising a step of treating the stem cells with the substance that inhibits BMP signaling during the first few days of the differentiation-inducing stage.

(6) A method according to any one of (1) through (4) above, comprising a step of treating the stem cells with the substance that inhibits BMP signaling during pre-differentiation stage.

(7) A method according to any one of (1) through (4) above, comprising a step of treating the stem cells with the substance that inhibits BMP signaling during pre-differentiation stage, and a step of treating the stem cells with the substance that inhibits BMP signaling during the first few days of the differentiation-inducing stage.

(8) A method according to any one of (1) through (7) above, wherein the substance that inhibits BMP signaling is a BMP antagonist.

(9) The method according to (8) above, wherein the BMP antagonist is one or more selected from the group comprising Noggin, Chordin, fetuin, follistatin, sclerostin, DAN, Cerberus, gremlin, Dante and related proteins thereof.

(10) A method according to any one of (1) through (9) above, wherein the stem cells are mammalian cells having the ability to differentiate into cardiomyocytes in vitro.

(11) The method according to (10) above, wherein the mammalian cells having the ability to differentiate into cardiomyocytes are pluripotent stem cells or cells derived therefrom.

(12) The method according to (11) above, wherein the pluripotent stem cells are embryonic stem cells, cells having similar properties to embryonic stem cells, embryonic germ cells, or multipotent adult progenitor cells.

(13) The method according to (12) above, wherein the pluripotent stem cells are embryonic stem cells.

(14) A method according to (1) through (13) above, wherein the stem cells are derived from human.

(15) A method for production of cardiomyocytes comprising a method according to any one of (1) through (14) above.

(16) Cardiomyocytes obtained by a method according to any one of (1) through (14) above.

(17) A method for treating heart conditions stemming from the debility, functional failure or death of cardiomyocytes, consisting of the administration (transplantation) of cardiomyocytes according to (16) above in or around a site of weakening, functional failure or death of cardiomyocytes.

(18) A method of screening for substances useful in treating heart conditions stemming from the weakening, functional failure or death of cardiomyocytes, consisting of bringing a test substance into contact with cardiomyocytes according to (16) above, and measuring qualitative or quantitative changes in cell functions or the differentiation efficiency of the cells into cardiomyocytes.

(19) A drug composition or support for the treatment of heart conditions stemming from the weakening, functional failure or death of cardiomyocytes, comprising cardiomyocytes according to (16) above as an active component.

As the stem cell source for preparing cardiomyocytes, the inventors used pluripotent stem cells, especially ES cells, which were most commonly used, and as a result of extensive research into the conditions for inducing differentiation into cardiomyocytes or precursor cells, they made the present invention when they discovered that when a substance that inhibits BMP (bone morphogenic protein) signaling was added to the medium during a certain, restricted stage of culture, populations of cells having beating ability which were identified as cardiomyocytes were developed much more selectively and efficiently than in conventional methods, and also discovered that addition of an excess amount of BMP resulted in a dramatic reduction in the myocardial differentiation-inducing effect of treatment with the substance that inhibits BMP signaling, showing that inhibition of BMP signaling positively induces differentiation of pluripotent stem cells into cardiomyocytes.

In the present invention, a substance that inhibits BMP signaling is a substance having the effect of blocking or competing BMP signaling, and examples include BMP antagonists, specific neutralizing antibodies to BMP family molecules, solubilized (non-cell membrane anchoring type) BMP receptor molecules and the like. Other examples include gene expression vectors, specific antisense oligo-nucleotides, ribozymes, antisense RNA for RNA interference, low molecular weight compounds and the like which either suppress or arrest expression of BMP family molecules or the functional gene products of their receptor genes, or else suppress or arrest expression of genes which code trans-activating components of the BMP signaling pathway.

Beating cells prepared from pluripotent stem cells by the method of the present invention are cells having the characteristics of "cardiomyocytes", and for example expression of genes for GATA-4, TEF-1, Tbx-5, MEF2, MLC-2v and other myocardial-specific transcription factors and expression of proteins such as the myocardial-specific markers sarcomeric myosin, troponin I, α-actinin, ANP and the like can be confirmed therein.

In addition to the commonly used floating aggregation culture method, the hanging drop culture method or a co-culture method using feeder cells can be used as the method for inducing differentiation of pluripotent stem cells in the present invention.

It was also discovered from an investigation of the adequate time-points and periods for adding the substance that inhibits BMP signaling, when pluripotent stem cells are dispersed as single cells or cell aggregates consisting of small number of cells, and differentiation is induced by a method such as floating aggregation culture or co-culture with feeder cells, it is more effective either to pre-treat the pluripotent stem cells with a BMP antagonist before differentiation, or to treat with it only during a few days immediately after initiation of culture for inducing differentiation, or to combine these two techniques. It has been shown that if the BMP antagonist is continuously present during the entire time of floating culture, co-culture with feeder cells or the like, the efficiency of cardiomyocyte differentiation from pluripotent stem cells is greatly reduced.

That is, the present invention relates to a method of inducing differentiation of pluripotent stem cells into cardiomyocytes, wherein stem cells are cultured under the transient treatment of a substance that inhibits BMP signaling.

In the present invention, stem cells having myocardial differentiation ability are cells having the ability to potentially differentiate into cardiomyocytes in an in vitro culture, and examples include pluripotent stem cells, mesenchymal stem cells, CMG cells, Spoc cells and the like. Pluripotent stem cells are cells which can proliferate indefinitely or for a long period of time while remaining in an undifferentiated state in an in vitro culture, which exhibit normal karyotypes, and which have the ability to differentiate into all three germ layers (ectoderm, mesoderm, and endoderm) under appropriate conditions, and examples include ES cells, ES-like cells, EG cells, MAPC and the like.

A different embodiment of the present invention relates to cells which exhibit the morphological, physiological and/or immunological characteristics of cardiomyocytes and which have been derived from pluripotent stem cells. In terms of physiological and/or immunological properties, cells prepared by the method of the present invention may express one or more markers specific to cardiomyocytes which are recognized as cardiomyocytes, but this is not a limitation.

The present invention also relates to a method of screening using cells prepared by the method of the present invention to identify potential chemotherapy drugs or novel factors which promote the development, differentiation, regeneration, survival and the like of cardiomyocytes.

The present invention also relates to a kit for inducing differentiation of pluripotent stem cells into cells having the morphological, physiological and/or immunological properties of myocardial precursor cells or cardiomyocytes. This kit is useful for implementing the method of the present invention.

Another embodiment of the present invention relates to a method for treating hearts suffering from cardiac disorders using cells prepared by the method of the present invention, and to a heart disease treatment drug having cells prepared by the method of the present invention as an active component.

These advantages and other advantages and characteristics of the present invention are adequately described in the following detailed explanation of preferred embodiments.

Anyone implementing the present invention can consult standard references regarding ordinary methods of cell culture and developmental and cell biological studies using pluripotent stem cells. These include Guide to Techniques in Mouse Development (Wasserman et al Eds., Academic Press, 1993); Embryonic Stem Cell Differentiation in vitro (M. V. Wiles, Meth. Enzymol. 225:900, 1993); Manipulating the Mouse Embryo: A laboratory manual (Hogan et al Eds., Cold Spring Harbor Laboratory Press, 1994); and Embryonic Stem Cells (Turksen Ed., Humana Press, 2002). The reagents and kits for cell culture and developmental and cell biological studies cited in these Specifications can be obtained from commercial sources including Invitrogen/GIBCO, Sigma and the like.

Myocardial precursor cells and cardiomyocytes can be efficiently and selectively produced from stem cells using the method of the present invention. Myocardial (precursor) cells prepared in this way can be used to search for and develop effective drugs for treating heart disease, and could potentially be applied to myocardial transplantation therapy for severe heart disease.

Figure 1A:
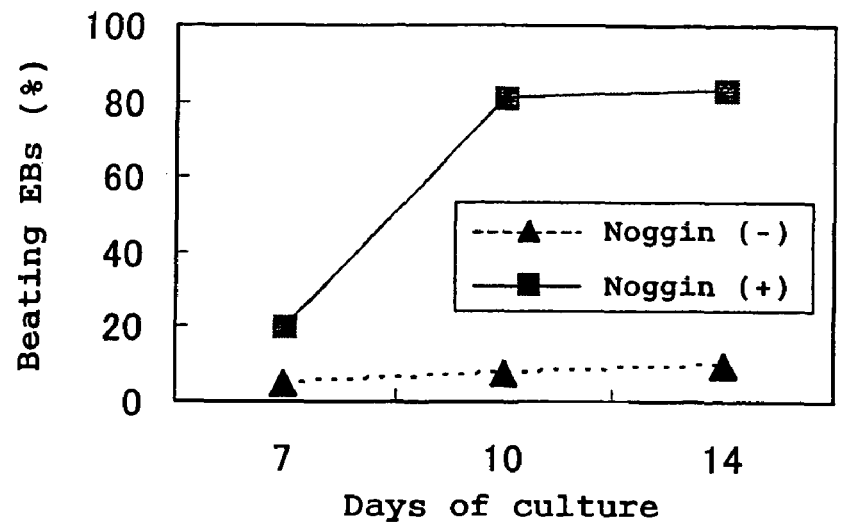
FIG. 1A shows the effects of addition of the Noggin protein (500 ng/mL) on the appearance rate of beating EBs derived from ES cell (EB3) using floating culture method.

In this disclosure, "cardiomyocytes" include cardiac precursor cells having the ability to become functional cardiomyocytes in the future, as well as fetal and adult cardiomyocytes at all stages of differentiation, and are defined as cells that can be identified by one or preferably more than one of the following methods using one or preferably more than one marker or index.

The expression of various markers specific to cardiomyocytes is detected by conventional biochemical or immunochemical methods. There is no particular limit on the method, but preferably an immunochemical method such as immunocytochemical staining or immuno-electrophoresis is used. In these methods, marker-specific polyclonal antibodies or monoclonal antibodies can be used which react with cardiac precursor cells or cardiomyocytes. Antibodies for individual specific markers are commercially available, and can be easily used. Markers specific to cardiac precursor cells or cardiomyocytes include for example myosin heavy/light chains, α-actinin, troponin I, ANP, GATA-4, Nkx2.5, MEF-2c and the like.

Alternatively, although the method is not particularly limited, expression of cardiac precursor cell-specific or cardiomyocyte-specific marker genes can also be confirmed by reverse transcriptase polymerase chain reaction (RT-PCR) or hybridization analysis, molecular biological methods which have been commonly used in the past for amplifying, detecting and analyzing mRNA coding for any marker proteins. The nucleic acid sequences coding for markers specific to cardiac precursor cells and cardiomyocytes (such as myosin heavy/light chains, α-actinin, troponin I, ANP, GATA-4, Nkx2.5 and MEF-2c) are already known and are available through public data bases such as GenBank, and the marker-specific sequences needed for use as primers or probes can be easily determined.

Physiological indexes can also be used additionally to confirm differentiation of pluripotent cells into cardiomyocytes. For example, useful markers include spontaneous beating by cells derived from pluripotent cells, expression of various ion channels and the ability to react to electrophysiological stimulus.

Pluripotent stem cells that can be used in the present invention include ES cells, EG cells, MAPC and the liked derived from mammals such as mice, monkeys and humans that are already widely used as culture cells. Specific examples of mouse-derived ES cells include EB3 cells, E14-cells, D3 cells, CCE cells, R1 cells, 129SV cells, J1 cells and the like. Standard protocols have also been established for preparing, subculturing and preserving ES cells, EG cells and MAPC, and in addition to the references cited above, the operator can easily obtain such pluripotent stem cells by consulting various other references (Matsui et al, Cell 70:841, 1992; Shamblott et al., Proc. Natl. Acad. Sci. USA 95:13726, 1998; U.S. Pat. No. 6,090,622; Jiang et al, Nature 418:41, 2002; International Patent Disclosure 01/11011).

Cells which can be used in the present invention are not limited to the aforementioned three types, and include all pluripotent stem cells derived from mammalian embryos and fetuses, umbilical cord bloods, or adult tissues, blood and the like such as adult organs and bone marrow. Specific examples include stem cells obtained by treating root sheath cells or epidermal cells with a drug such as 5-azacytidine (Sharda & Zahner, International Patent Disclosure 02/051980), stem cells obtained by treating monocytes with CR3/43 antibodies (Abuljadayel, Curr. Med. Res. Opinion 19:355, 2003), and stem cells that are characteristically similar to ES cells, such as stem cells derived from adult inner ear cells (Li et al, Nature Med., Advance online publication). In this case, characteristical similarity to ES cells is defined in terms of cytobiological properties unique to ES cells, such as the presence of ES cell-specific surface markers (antigen), the expression of ES cell-specific genes, or the ability to produce teratomas or chimera mice.

Even cells having a characteristic different from that of ES cells or cells other than pluripotent stem cells can be used in the methods described in the present invention if they are cells having properties which allow them to differentiate into cells having a cardiomyocyte-like features in vitro. Examples of such cells include bone marrow mesenchymal stem cells derived from bone marrow cells (Bruder et al, U.S. Pat. No. 5,736,396; Pittenger et al, Science 284:143, 1999), CMG cells (Makino et al, J. Clin. Invest. 103:697, 1999; International Patent Disclosure 01/048151) and Spoc cells derived from muscle tissue (International Patent Disclosure 03/035382).

Any method suited to inducing differentiation of cardiomyocytes can be used as the culture method for preparing cardiomyocytes from pluripotent stem cells in the present invention, and for example using ES cells examples include floating aggregate culture, hanging drop culture, co-culture with supporting cells, gyratory culture, soft agar culture, micro-carrier culture and the like. In the case of floating aggregate culture for example, a specific example is a method of suspending ES cells as single cells (individual cells dispersed in a liquid phase with no adhesion between cells due to enzyme digestion or the like) in medium to a cell density of preferably 10 cells/mL to $1 \times 10^7$ cells/mL or more preferably 100 cells/mL to $1 \times 10^6$ cells/mL, seeding them on a culture plate, and culturing them for 4 to 30 days or preferably 6 to 15 days at 37° C. under $CO_2$ conditions of 5% carbon dioxide ventilation.

In a different embodiment using a co-culture method with supporting cells, the supporting cells are not particularly limited but are preferably cells having the characteristics of mesenchymal cells and more preferably cells having bone marrow stroma cell-like properties, such as ST2 cells, OP9 cells, PA6 cells or the like. These supporting cells are cultured to a high density and made into a feeder by a method such as mitomycin C treatment, irradiation or the like, and ES cells suspended as single cells in medium to a cell density of 1 cell/mL to $1 \times 10^6$ cells/mL or preferably 100 cells/mL to $1 \times 10^5$ cells/mL or more preferably $1 \times 10^3$ cells/mL to $1 \times 10^4$ cells/mL are seeded thereon and cultured for 4 to 30 days or preferably 6 to 15 days at 37° C. under $CO_2$ conditions of 5% carbon dioxide ventilation.

In the present invention, a substance that inhibits BMP signaling is a substance that has the effect of blocking or interrupting BMP signaling, and examples include BMP antagonists, specific neutralizing antibodies to BMP family molecules, solubilized (non-cell membrane anchoring type) BMP receptor molecules and the like. Other examples include gene expression vectors, specific antisense oligonucleotides, ribozymes, antisense RNA for RNA interference, low molecular weight compounds and the like which either suppress or arrest expression of BMP family molecules or the functional gene products of their receptor genes or else suppress or arrest expression of genes which code transactivating components of the BMP signaling pathway.

A BMP antagonist is defined as a substance which binds to a BMP family molecule (such as BMP-2, BMP-4, BMP7 or the like) and blocks or inhibits binding of the BMP molecule with a BMP receptor on the cell surface, or a substance which causes suppression or interruption of BMP signaling by binding to a BMP receptor. Examples of preferred BMP antagonists in the present invention include Noggin, Chordin and the like. Other examples include Noggin-related proteins or Chordin-related proteins having 80% or more or preferably 90% or more homology with the amino acid sequence of the relevant protein and having the activity of BMP antagonists. A Noggin-related protein or Chordin-related protein coded for by nucleotides that hybridize under stringent conditions (for example, 2×SSC) with nucleotides encoding for Noggin or Chordin is also included in the same way.

The present invention features the culture of pluripotent stem cells under the stimulus of a substance that temporarily inhibits BMP signaling, and while the stimulus method is not particularly limited, a method of adding a purified recombinant protein to culture medium is preferred. However, any other method can be used which has the same effects as the method of adding a substance that inhibits BMP signaling to culture as a purified recombinant protein. Examples include a method of adding Noggin or another BMP antagonist which has been extracted and purified from living tissues, a method of introducing a gene expression vector for Noggin or another BMP antagonist into the pluripotent stem cells themselves, a method of introducing a gene expression vector for Noggin or another BMP antagonist into supporting cells and using those transfected cells as co-culture cells and a method using a culture supernatant or other cell product of those transfected cells and the like, all of which are included as part of the embodiment for adding a BMP antagonist in medium in the method of the present invention.

In implementing the present invention, the protein and gene of the substance used to inhibit BMP signaling are preferably derived from animals of the same species as that used to derive the pluripotent stem cells. For example when implementing the present invention using mouse pluripotent stem cells, a purified recombinant protein (Recombinant Mouse Noggin/Fc Chimera; R&D Systems, Genzyme Technology) prepared from mouse-derived cells in which a fused gene consisting of mouse Noggin cDNA linked to immunoglobulin constant (Fc) region cDNA is introduced and expressed is commercially available, and can be easily used as a mouse-derived Noggin protein. Those derived from animals of another species can also be used, however, and a purified recombinant protein (PeproTech) prepared by introducing and causing expression of human Noggin cDNA in *E. coli* can be substituted. Noggin proteins derived from pigs, sheep, horses, birds (such as chickens) or amphibians (such as Xenopus) can also be used. Similar proteins can be used for Chordin and other BMP antagonists. The nucleotide sequences of the genes coding for these factors are available from public DNA data bases such as that of the U.S. National Center for Biotechnology (NCBI), and the cDNA of these genes can be obtained and used by someone skilled in the art. For example, the human and mouse genes for Noggin and Chordin have already been identified, and the nucleotide sequences for human Noggin, mouse Noggin, human Chordin and mouse Chordin are recorded in the NCBI data base as NM#005450, NM#008711, NM#073411 and NM#009893, respectively.

A BMP antagonist in the present invention may be a substance which binds to a BMP molecule (such as BMP-2, BMP-4, BMP-7 or the like) and which blocks or inhibits binding of the BMP molecule with a BMP receptor on the cell surface or a substance which causes suppression or interruption of BMP signaling by binding with a BMP receptor, and typical examples include Noggin (Re'em-Kalma et al, Proc. Natl. Acad. Sci. USA 92:12141, 1995; Zimmerman et al, Cell 86:599, 1996) and Chordin (Piccolo et al, Cell 86:589, 1996; De Robertis et al, U.S. Pat. No. 5,679,783; LaVallie et al, U.S. Pat. No. 5,846,770; Lavallie et al, U.S. Pat. No. 5,986,056). Specific examples of other BMP antagonists include follistatin, fetuin, sclerostin and molecules belonging to the DAN/Cerberus family, such as DAN, Cerberus, gremlin, Dante and the like (Balemans & Hul, Dev. Biol. 250:231, 2002). Synthetic or recombinant analogues of naturally occurring BMP antagonists are also useful in implementing the present invention.

Methods of treating pluripotent stem cells in implementing the present invention are not limited to methods using Noggin and other BMP antagonists, and a method having the same effects as a BMP antagonist or in other words a method which causes inhibition of BMP signaling may also be used. Specific examples of methods that cause inhibition of BMP signaling include methods using specific neutralizing antibodies to BMP family molecules and methods using solubilized (non-cell membrane anchoring type) BMP receptor molecules. Other examples include methods of introducing into the cells gene expression vectors, specific antisense oligonucleotides, ribozymes, antisense RNA for RNA interference, low molecular weight compounds and the like which either suppress or arrest expression of BMP family molecules or the functional gene products of their receptor genes or else suppress or arrest expression of genes which code transactivating components of the BMP signaling pathway.

When using a substance that inhibits BMP signaling (such as Noggin, Chordin or another BMP antagonist) with pluripotent stem cells in the present invention, the period for applying these factors can be divided into two stages. These are the stages before and after the pluripotent stem cells are dispersed either as individual cells or as cell masses consisting of small numbers of cells, and floating aggregate cultured or co-cultured with supporting cells or the like, and the former stage is called the pre-differentiation stage below while the latter stage is called the differentiation-inducing stage.

In the pre-differentiation stage, the substance that inhibits BMP signaling in pluripotent stem cells is applied beginning 1 to 2 days before or preferably 3 days or more before the EBs are formed to induce differentiation.

Moreover, in the pre-differentiation stage the ES cells are preferably cultured under ordinary conditions suited to the type of animal to maintain them in an undifferentiated state. That is, in the case of mouse ES cells it is desirable to add leukemia inhibitory factor (LIF) to the medium at a concentration of 100 to 10,600 U/mL or preferably 500 to 2000 U/mL.

The substance that inhibits BMP signaling does not need to be applied during the entire culture period, and for example when a BMP antagonist such as Noggin or Chordin is used as the substance that inhibits BMP signaling, culture in medium in which the BMP antagonist is present in an active state is preferably limited to within the first 5 days or more preferably the first 3 days of the differentiation-inducing period. However, the times during which the substance which inhibits BMP signaling is applied may be varied appropriately depending on conditions such as the animal from which the cells are derived, the cell strain used, the mode of differentiation induction and the type of substance used to inhibit BMP signaling.

When a BMP antagonist (such as the Noggin protein or Chordin protein) is used as the substance that inhibits BMP signaling in implementing the present invention, the old medium is sterilely removed and replaced with medium containing the Noggin protein or Chordin protein at a concentration of 1 ng/mL to 2 μg/ml or preferably 5 ng/mL to 1000 ng/mL or more preferably 10 ng/mL to 500 ng/mL, and culture is preferably continued for several days. When using another substance that inhibits BMP signaling, the concentration can be varied appropriately depending on the type of substance.

Cardiomyocytes derived from ES cells or other pluripotent stem cells by the aforementioned methods can be further collected, isolated and purified by known methods to efficiently obtain large quantities of highly pure cardiomyocytes. The cardiomyocytes thus obtained are hereafter called cardiomyocytes prepared according to the present invention.

Any known method of cell isolation and purification can be used as the method of purifying the cardiomyocytes, and specific examples include flow cytometry, magnetic beads, panning and other methods involving antigen-antibody reactions (see Monoclonal Antibodies: principles and practice, Third Edition (Acad. Press, 1993); Antibody Engineering: A Practical Approach (IRL Press at Oxford University Press, 1996) as well as cell fractioning by density gradient centrifugation using a carrier such as sucrose, Percoll or the like. Another method of selecting cardiomyocytes is to first artificially introduce a modification into the genes of the ES cells or other pluripotent stem cells, making them drug resistant or capable of ectopic protein expression, and collecting cells having the morphology of cardiomyocytes. For example, by introducing a gene cassette capable of expressing a neomycin (G418) resistance gene under the control of the α-myosin heavy chain promoter into mouse ES cells, Field and his co-researchers succeeded in constructing a system in which ES cells were differentiated into cardiomyocytes and only those cells which expressed the α-myosin heavy chain gene could survive in medium to which G418 had been added, and 99% or more of the cells selected as G418-resistant cells by this method were confirmed to be cardiomyocytes ((U.S. Pat. No. 6,015,671, Specifications; Klug et al, J. Clin. Invest. 98: 216, 1996).

Cardiomyocytes prepared according to the present invention are useful in pharmacological evaluations and activity evaluations of various bioactive substance (for example, drugs) and novel gene products of unknown function. For example, they can be used to screen for substances and drugs involved in controlling the differentiation of cardiomyocytes from ES cells and other pluripotent stem cells, for substances and drugs involved in regulating the function of cardiomyocytes, and for substances and drugs which are toxic or inhibitory towards cardiomyocytes. In particular, there are currently very few methods of screening using human cardiomyocytes, and the cardiomyocytes prepared according to the present invention provide a useful source of cells for implementing such screening methods. In another mode, an evaluation kit comprising cardiomyocytes prepared according to the present invention is also useful for such screening.

Test substances to be screened may include any which can be added to culture, such as low-molecular-weight compounds, high-molecular-weight compound, organic compounds, inorganic compounds, proteins, peptides, genes, viruses, cells, cell culture liquids, microbial culture liquids and the like. Efficient methods of introducing genes into culture systems include methods of addition to culture systems using retroviruses, adenoviruses and other virus vectors as well as methods of addition after insertion into liposomes and other artificial constructs.

The test substance can be evaluated by measuring the efficiency of induction of differentiation from ES cells or other pluripotent stem cells into cardiomyocytes, or the qualitative or quantitative changes in myocardial cell functions. For example, the myocardial differentiation induction efficiency of a test substance can be measured by using biochemical or immunochemical means to detect the expression of various cardiomyocyte-specific markers in pluripotent stem cells cultured using methods according to the present invention after they have been culture for 5 to 15 or preferably 7 to 12 days. There are no particular limits on the biochemical or immunochemical means, but preferably an immunochemical method such as immunocytochemical staining or immunoelectrophoresis can be used. Marker-specific polyclonal antibodies or monoclonal antibodies that bind to the cardiomyocytes can be used in these methods. Antibodies that target individual specific markers are commercially available and can be easily used. Examples of cardiomyocyte-specific markers include myosin heavy and light chains, α-actinin, troponin I, ANP, GATA-4, Nkx2.5, MEF-2c and the like.

Myocardial cell survival is one example of a myocardial cell function that can be used as a marker for evaluating a test substance. Specifically, apoptosis (cell death) can be induced by seeding cardiomyocytes prepared by the method according to the present invention on a culture plate to an appropriate cell density and culturing them in serum-free medium, and in this case a suitable amount of the test substance can be added to the medium and the survival rate or death rate of cardiomyocytes can be measured. The survival rate or death rate of the cardiomyocytes can be measured by macroscopic observation using incorporation of a dye such as trypan blue as the marker, by a method using dehydrogenase activity (reduction activity) as the marker, or by a method using annexin V expression or caspase activity, which are specific to apoptosis cells, as the marker. Kits exploiting these mechanisms are available from many manufacturers including Sigma, Clonetech and Promega, and are easy to use.

Because a substance or drug obtained by such a screening method acts to induce differentiation of cardiomyocytes and regulate their functions, it can be used for example as a preventative or therapeutic drug for heart conditions including myocardial infarction, ischemic heart disease, congestive heart failure, hypertrophic cardiomyopathy, dilative cardiomyopathy, myocarditis, chronic heart failure and the like. These compounds may be novel compounds or known compounds.

Moreover, cardiomyocytes prepared according to the present invention can be used as myocardial regeneration drugs or heart disease treatment drugs. Examples of heart disease include myocardial infarction, ischemic heart disease, congestive heart failure, hypertrophic cardiomyopathy, dilative cardiomyopathy, myocarditis, chronic heart failure and the like. When used as myocardial regeneration drugs or heart disease treatment drugs, cardiomyocytes prepared according to the present invention can be included in any form as long as the purity is high, such as cells floating in a medium or other aqueous carrier, cells embedded in a biodegradable substrate or other support, or cells made into a single-layer or multilayer myocardial sheet (Shimizu et al, Circ. Res. 90:e40, 2002).

Although not particularly limited to these, methods for transporting the aforementioned therapeutic drug to a damage site include direct injection into the heart via an open chest or syringe, methods of transplantation via a surgical incision in the heart, and methods of transplantation via the blood vessels using a catheter (Murry et al, Cold Spring Harb. Symp. Quant. Biol. 67:519, 2002; Menasche, Ann. Thorac. Surg. 75:S20, 2003; Dowell et al, Cardiovasc. Res. 58:336, 2003). Extremely good therapeutic effects have been reported when cardiomyocytes collected from a fetal heart were transplanted by such methods to the hearts of animals with heart damage (Menasche, Ann. Thorac. Surg. 75:S20, 2003; Reffelmann et al, Heart Fail. Rev. 8:201, 2003). Cardiomyocytes derived from ES cells have characteristics extremely similar to those of cardiomyocytes derived from fetal hearts (Maltsev et al, Mech. Dev. 44:41, 1993; Circ. Res. 75:233, 1994). Moreover, an extremely high take rate equivalent to that achieved with fetal myocardial transplantation has been confirmed in animal experiments in which cardiomyocytes derived from ES cells were actually transplanted into adult hearts (Klug et al, J. Clin. Invest. 98:216, 1996). Consequently, it is expected that supplementary transplantation of cardiomyocytes prepared according to the present invention into diseased heart tissue should stimulate improved heart functions in cases of the aforementioned heart diseases stemming from damage or loss of heart cells.

EXAMPLES

The present invention is explained in more detail below using examples, but these examples only serve to illustrate the present invention and do not limit its scope.

Example 1

Effects of Noggin Treatment on Cardiomyocyte-Differentiation from ES Cells

The effects of addition of the Noggin protein to culture medium on the development of cardiomyocytes were studied in an experimental system in which EBs were formed by floating aggregation culture (called simply floating culture in the examples of this application below) of ES cells and induced to differentiate into cardiomyocytes.

In the experiments below, EB3 cells (provided by Prof. Hitoshi Niwa of Riken, Japan), R1 cells (provided by Andrew Nagy of Mount Sinai Hospital, Canada) and 129SV cells (purchased from Dainippon Pharmaceutical Co.) were used as the ES cells, but in general there were no differences between these ES cell lines. These ES cells were passaged and maintained in an undifferentiated state according to the methods described in Manipulating the Mouse Embryo: A Laboratory Manual (Hogan et al Eds., Cold. Spring Harbor Laboratory Press, 1994), Embryonic Stem Cells: Methods and Protocols (Turksen Ed., Humana Press, 2002) and the like, using Glasgow Minimum Essential Medium (GMEM, Sigma) containing 10% fetal bovine serum (FBS), 0.1 mM MEM non-essential amino acids, 2 mM L-glutamine and 0.1 mM 2-mercaptoethanol to which 2000 U/mL of leukemia inhibitory factor (LIF) (ESGRO; Chemicon) had been added.

3 days before the starting of floating culture, ES cells which had formed colonies under the aforementioned conditions were washed twice with PBS, dispersed into single cells by treatment with an 0.25% trypsin solution comprising 1 mM EDTA, and prepared as a $2.5 \times 10^5$ cells/mL cell suspension using α-modified Minimum Essential Medium (a MEM, Sigma) comprising 10% FBS, 0.1 mM MEM non-essential amino acids, 2 mM L-glutamine and 0.1 mM 2-mercaptoethanol (hereunder called the "differentiation medium") in the presence of 2000 U/mL of LIF. 500 ng/mL of Recombinant Mouse Noggin/Fc Chimera protein (R&D Systems, hereunder called "the Noggin protein") was added or not to this suspension, which was then seeded on gelatin-coated commercially available cell culture plates (T75 flask, Greiner) in the case of the EB3 cell, which is a non-feeder-dependent ES cell line. In the case of the feeder-dependent cell strain R1 and 129SV, a gelatin-coated plate seeded with mitomycin-treated mouse embryonic fibroblasts (Dainippon Pharmaceutical) was prepared in advance to provide feeder cells on which the cell suspension was then seeded.

Floating culture was performed as follows to form EBs from the ES cells. ES cells which had been cultured for 3 days in differentiation medium with or without the addition of Noggin were washed twice with PBS, dispersed into single cells by treatment with an 0.25% trypsin solution comprising 1 mM EDTA, and plated at a concentration of $1 \times 10^2$ cells/mL or $2 \times 10^5$ cells/mL into commercially available Petri dishes with low cell attachment (dia. 100 mm; Valmalk). Three days before floating culture start, 500 ng/mL of Noggin protein was added to the medium in some groups. The cells were then maintained while preventing attachment to the plate, and floating culture was done for 4 to 14 days. Under these experimental conditions the ES cells started to aggregate and form EBs immediately after the start of floating culture, and autonomous beating was observed in some of the EBs from about the $7^{th}$ to $8^{th}$ day of culture.

As a different way of EBs formation from ES cells, a hanging drop culture was also performed as follows. ES cells which had been cultured for 3 days in differentiation medium with or without Noggin were washed twice with PBS, and dispersed into single cells by treatment with 0.25% trypsin solution comprising 1 mM EDTA. Next, drops were prepared comprising 500 cells in 15 µL of differentiation medium, suspended from the lids of culture plate and cultured for 4 days. At this time, 500 ng/mL of Noggin protein was added to the medium of the ES cell groups pre-treated with Noggin for 3 days. After the hanging drop culture, the EBs that formed in the drops were plated onto commercially available cell culture dishes (4-well Multidish; Nunc) filled with differentiation medium and cultured in adhesion to induce cardiomyocyte differentiation. Following the adhesion culture, half the medium was replaced with fresh medium every 2 days. Under these experimental conditions, the ES cells were seen to aggregate and form EBs immediate after the start of hanging drop culture as in the floating culture, and spontaneous beating was observed in some of the EB-derived colonies from about the $3^{rd}$ to $4^{th}$ day of adhesion culture of the collected EBs ($7^{th}$ to $8^{th}$ day after start of hanging drop culture).

The percentage of EBs exhibiting spontaneous beating was investigated periodically as one of a useful index of the differentiation and development of cardiomyocytes from ES cells. When EB3 cells were used as the ES cells and cultured in suspension at a cell density of $1 \times 10^2$ cells/mL, very few of the EBs derived from ES cells not treated with Noggin (Noggin (−) group) exhibited beating even after 14 days of culture (FIG. 1A). On the other hand, beating was observed in EBs from Noggin-treated ES cells (Noggin (+) group) beginning on the $7^{th}$ day of floating culture, and beating was confirmed in 80% or more of EBs on the $14^{th}$ day. The same tendencies were seen when the cells were cultured in suspension at a concentration of $2 \times 10^5$ cells/mL, with beating ultimately observed in less than 10% of EBs in the Noggin (−) group, while EBs in the Noggin (+) group 30% or more exhibited beating on the $10^{th}$ day and 90% or more on the $14^{th}$ day. In the Noggin (−) EBs beating was limited to a certain restricted regions of the EBs, while in the Noggin (+) EBs, surprisingly, beating was observed throughout virtually all regions of the surface layer.

Figure 1B:
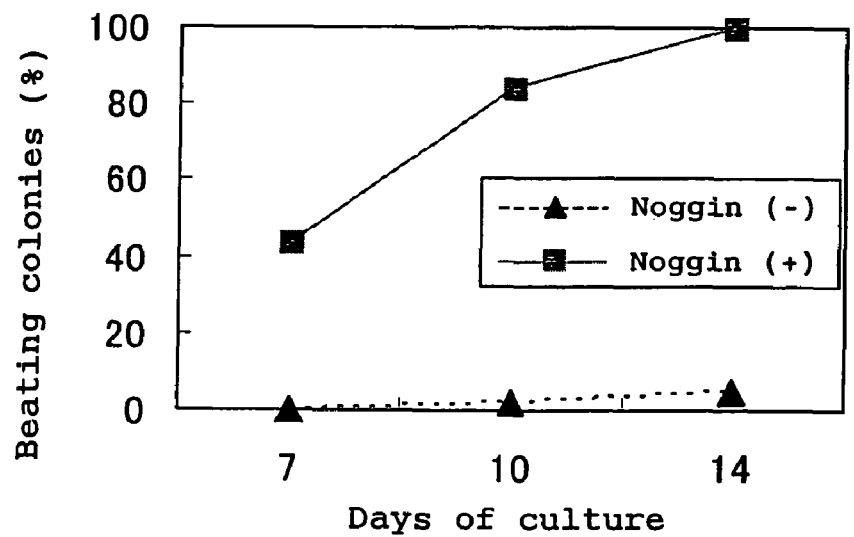
FIG. 1B shows the effects of addition of the Noggin protein (500 ng/mL) on the appearance rate of beating EBs derived from ES cell (EB3) using hanging drop method.

Even under hanging drop culture conditions, the myocardial differentiation ability of the Noggin (+) ES cells was much greater than that of the Noggin (−) ES cells, with beating observed in 40% or more of the EB-derived colonies on the $7^{th}$ day after EBs formation ($3^{rd}$ day of adhesion culture), in 80% on the $10^{th}$ day and in virtually all on the $14^{th}$ day (FIG. 1B). As was observed under the floating culture conditions, while in the Noggin (−) group beating was only observed in cells in some parts of the colonies formed by attachment of EBs to culture dishes, in the Noggin (+) group beating was observed in cells throughout almost all of the EB-derived colonies.

Recombinant proteins of various cytokines and growth factors such as IGF (insulin-like growth factor)-1, FGF (fibroblast growth factor)-2, BMP-2 and the like were also added to the medium under the same conditions as for Noggin treatment, but none exhibited myocardial induction effects equivalent to or greater than those of Noggin.

Figure 2:
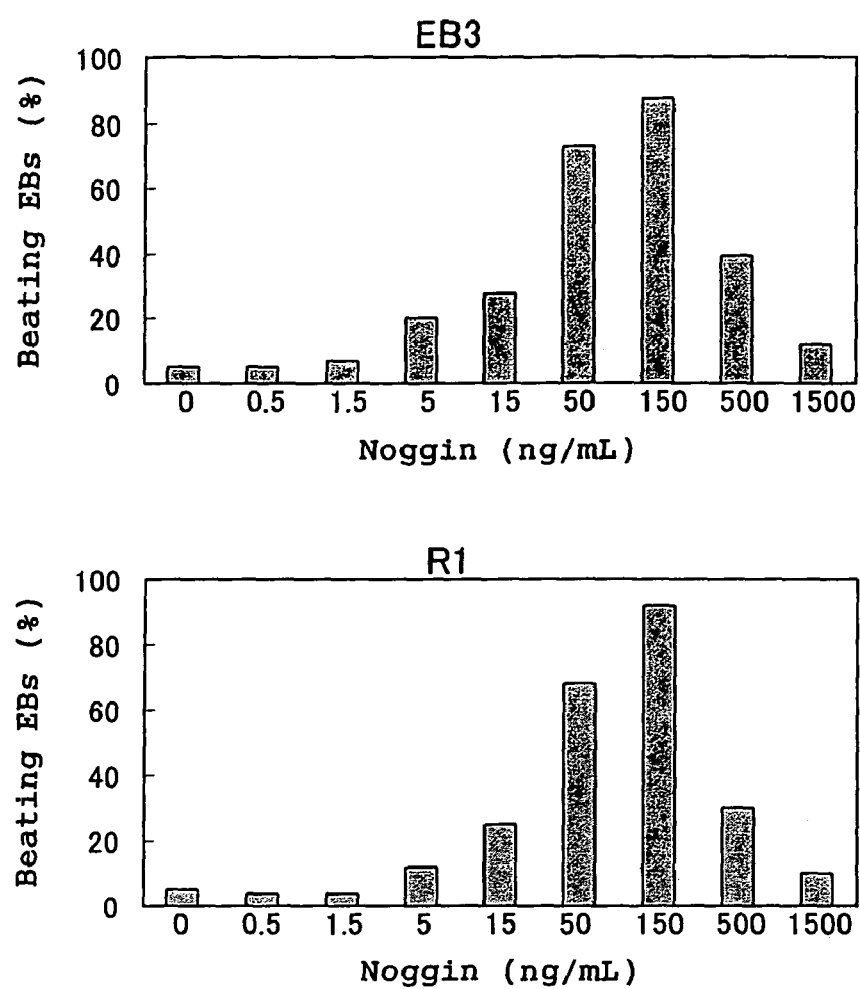
FIG. 2 shows the differences in the rate of appearance of beating EBs in the presence of various doses of Noggin. EBs were formed from ES cells (EB3 cells and R1 cells), and the rate of beating EBs was determined on the $10^{th}$ day of floating culture.

Next, we investigated how differences in the concentration of added Noggin protein would affect cardiomyocyte induction from ES cells. Cells were cultured according to floating culture method exactly the same conditions shown in FIG. 1, except that the concentration of the added Noggin protein was varied from 0.5 to 1500 ng/mL, as shown in FIG. 2. The EB3 cells and R1 cells exhibited almost the same dose-dependency, and the percentage of beating EBs was significantly greater than in the Noggin (−) group when the Noggin protein was added at concentrations of 5 ng/mL to 1500 ng/mL. In particular, a very good occurrence of beating EBs was obtained through addition of the Noggin protein at concentrations of 50 ng/mL to 150 ng/mL.

Example 2

Properties of Cardiomyocytes Derived from Noggin-Treated ES Cells

As shown in Example 1, beating of EBs prepared from ES cells was increased significantly by Noggin treatment, and to confirm that the beating cells in these EBs were cardiomyocytes, we investigated the expression of various myocardial-specific marker genes and proteins.

Figure 3:
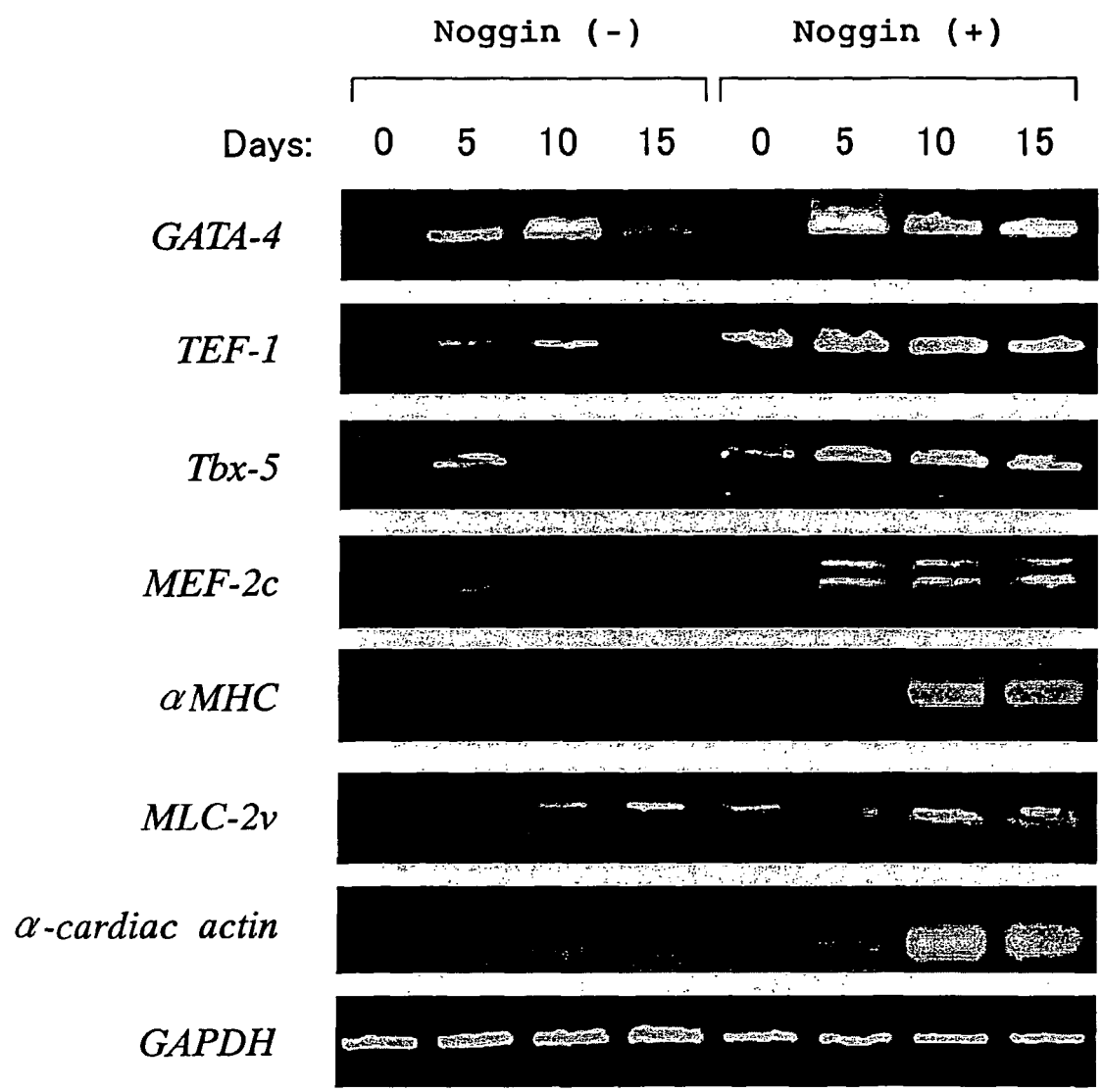
FIG. 3 shows the expression of myocardial-specific marker genes in Noggin-treated ES cells. EBs (derived from EB3 cells) were collected after 0, 5, 10 and 15 days of floating culture, and the expression of each gene was analysed. TEF-1: transcription enhancer factor-1, MEF-2c: muscle enhancement factor-2c, α-MHC: α-myosin heavy chain, MLC-2v: myosin light chain-2v, GAPDH: glyceraldehyde-3-phosphate dehydrogenase

Expression of various myocardial cell-specific marker genes in the Noggin (+) group and Noggin (−) group is shown in FIG. 3. EBs formed by floating culture as in FIG. 1 were collected periodically, and total RNA was prepared using RNeasy (Qiagen). Next, cDNA was reverse-transcribed by conventional methods using Superscript II (Invitrogen), and genes specific to cardiomyocytes were detected by polymerase chain reaction (PCR). The primers used to detect the transcripts of GATA-4, TEF-1, Tbx-5, MEF-2c, αMHC, MLC-2v, α-cardiac actin and GAPDH were as follows.

```
GATA-4 (forward)
5'-CTGTCATCTC ACTATGGGCA-3'         (SEQ ID NO: 1)

GATA-4 (reverse)
5'-CCAAGTCCGA GCAGGAATTT-3'         (SEQ ID NO: 2)

TEF-1 (forward)
5'-AAGACGTCAA GCCCTTTGTG-3'         (SEQ ID NO: 3)

TEF-1 (reverse)
5'-AAAGGAGCAC ACTTTGGTGG-3'         (SEQ ID NO: 4)

Tbx-5 (forward)
5'-GGAGCCTGAT TCCAAAGACA-3'         (SEQ ID NO: 5)

Tbx-5 (reverse)
5'-TTCAGCCACA GTTCACGTTC-3'         (SEQ ID NO: 6)

MEF-2c (forward)
5'-AGCAAGAATA CGATGCCATC-3'         (SEQ ID NO: 7)

MEF-2c (reverse)
5'-GAAGGGGTGG TGGTACGGTC-3'         (SEQ ID NO: 8)

αMHC (forward)
5'-GGAAGAGTGA GCGGCCATCA AGG-3'     (SEQ ID NO: 9)

αMHC (reverse)
5'-CTGCTGGAGA GGTTATTCCT CG-3'      (SEQ ID NO: 10)

-continued
MLC-2v (forward)
5'-GCCAAGAAGC GGATAGAAGG-3'         (SEQ ID NO: 11)

MLC-2v (reverse)
5'-CTGTGGTTCA GGGCTCAGTC-3'         (SEQ ID NO: 12)

α-cardiac actin (forward)
5'-CTGAGATGTC TCTCTCTCTC TTAG-3'    (SEQ ID NO: 13)

α-cardiac actin (reverse)
5'-ACAATGACTG ATGAGAGATG-3'         (SEQ ID NO: 14)

GAPDH (forward)
5'-TTCAACGGCA CAGTCAAGG-3'          (SEQ ID NO: 15)

GAPDH (reverse)
5'-CATGGACTGT GGTCATGAG-3'          (SEQ ID NO: 16)
```

PCR was performed with a GeneAmp PCR System 9600 (Perkin-Elmer) using TaKaRa Taq (Takara) as the heat-resistant DNA polymerase. First, PCR reaction solution comprising the cDNA was heated for 3 minutes at 94° C., followed by 30 cycles of 1 minute at 94° C., 1 minute at 55° C. and 1 minute at 72° C., and finally heated for 5 minutes at 72° C. and cooled to 4° C. The PCR product was electrophoresed with 3% polyacrylamide gel and stained with SYBR Green I (Takara), and a Molecular Imager FX (Bio-Rad) was used for detection.

As a result, while relatively weak expression of the GATA-4, TEF-1, Tbx-5, MLC-2v and other genes was seen from the $5^{th}$ through $10^{th}$ day of floating culture in the Noggin (−) group EBs, expression was seen from the first day (day 0) of culture in the Noggin (+) group EBs, and strong expression persisted from the $5^{th}$ through $15^{th}$ days thereafter. Expression of MEF-2c and myocardial-specific α-actin was seen beginning on the 5 day of culture, and the amount of expression was significantly greater in the Noggin (+) group EBs. Expression of the α-MHC (myosin heavy chain) gene was strong on the $10^{th}$ and $15^{th}$ days of culture in the Noggin (+) group EBs, but could not be confirmed in the Noggin (−) group EBs. These results show that Noggin treatment rapidly and strongly promoted differentiation of cardiomyocytes in EBs.

Expression of cardiomyocyte-specific marker proteins in the beating cells that developed in the Noggin (+) group EBs was also confirmed by immunocytochemical staining. Noggin (+) group EBs formed according to the same protocol as in FIG. 1 were collected on the $12^{th}$ day of culture and treated with 0.25% trypsin solution comprising 1 mM EDTA to disperse the cells. The dispersed cells were seeded at low densities on gelatin-coated cover slips so that the cells would not adhere to one another, and cultured in commercially available cell culture plates filled with differentiation medium. The next day, the cells on the cover slips were fixed with 4% paraformaldehyde solution, subsequently reacted with anti-sarcomeric myosin antibodies (MF20; American Type Culture Collection), anti-troponin antibodies (#sc-8120; Santa Cruz Biotechnology), anti α-actinin antibodies (#sc-15335; Santa Cruz) and anti-ANP antibodies (#AB5490; Chemicon) as the primary antibodies and then with Alexa488-labeled secondary antibodies (Molecular Probes), and observed under a fluorescence microscope.

Figure 4:
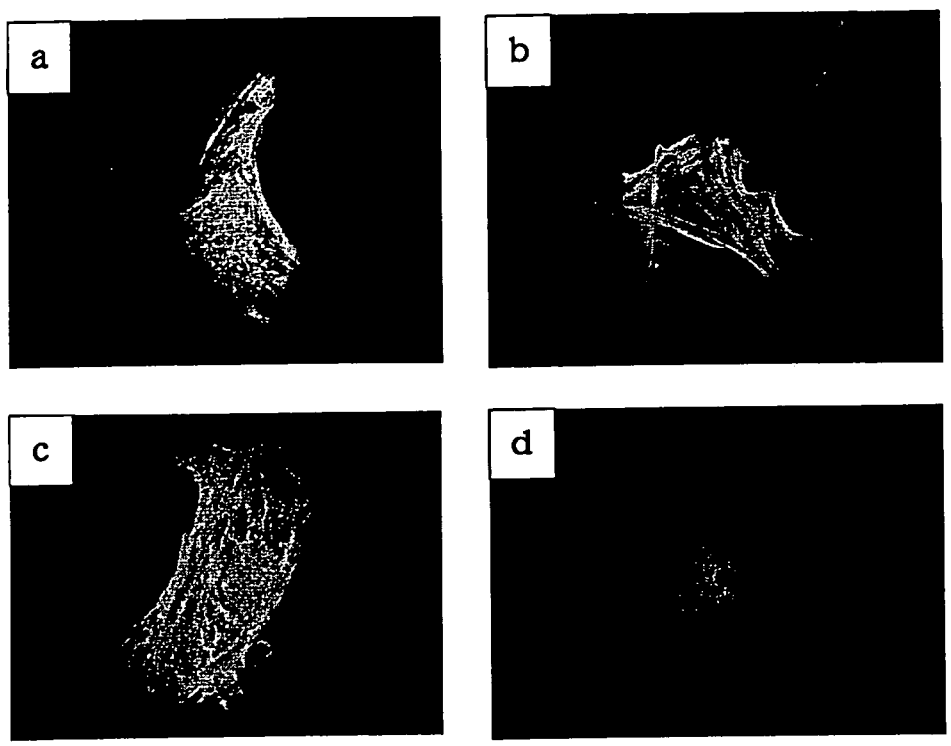
FIG. 4 shows the results of immunocytochemical staining of isolated cardiomyocytes from Noggin (+) group of EBs (derived from EB3 cells) on the $10^{th}$ day of floating culture. a: sarcomeric myosin, b: troponin I, c: α-actinin, d: ANP

As a result, numerous cells were found to be positive for the cardiomyocyte-specific marker proteins of sarcomeric myosin, troponin I, α-actinin and ANP (FIG. 4), proving that the beating cells derived from ES cells were cardiomyocytes.

Next, the distribution and proportion of cardiomyocytes in the EBs was confirmed using the same immunocytochemical staining as above. EBs collected on the $12^{th}$ day of floating culture were freshly embedded in a compound for preparing frozen sections (OCT Compound, Sakura Finetek USA Inc.) and then frozen with liquid nitrogen. The frozen samples were sectioned at 5 μm of thickness with a cryostat (Leica CM3050-S), and attached on glass slides. These frozen sections were reacted with antibodies to the aforementioned cardiomyocyte-specific markers, and marker protein positive cells were detected by the same methods as before.

Figure 5:
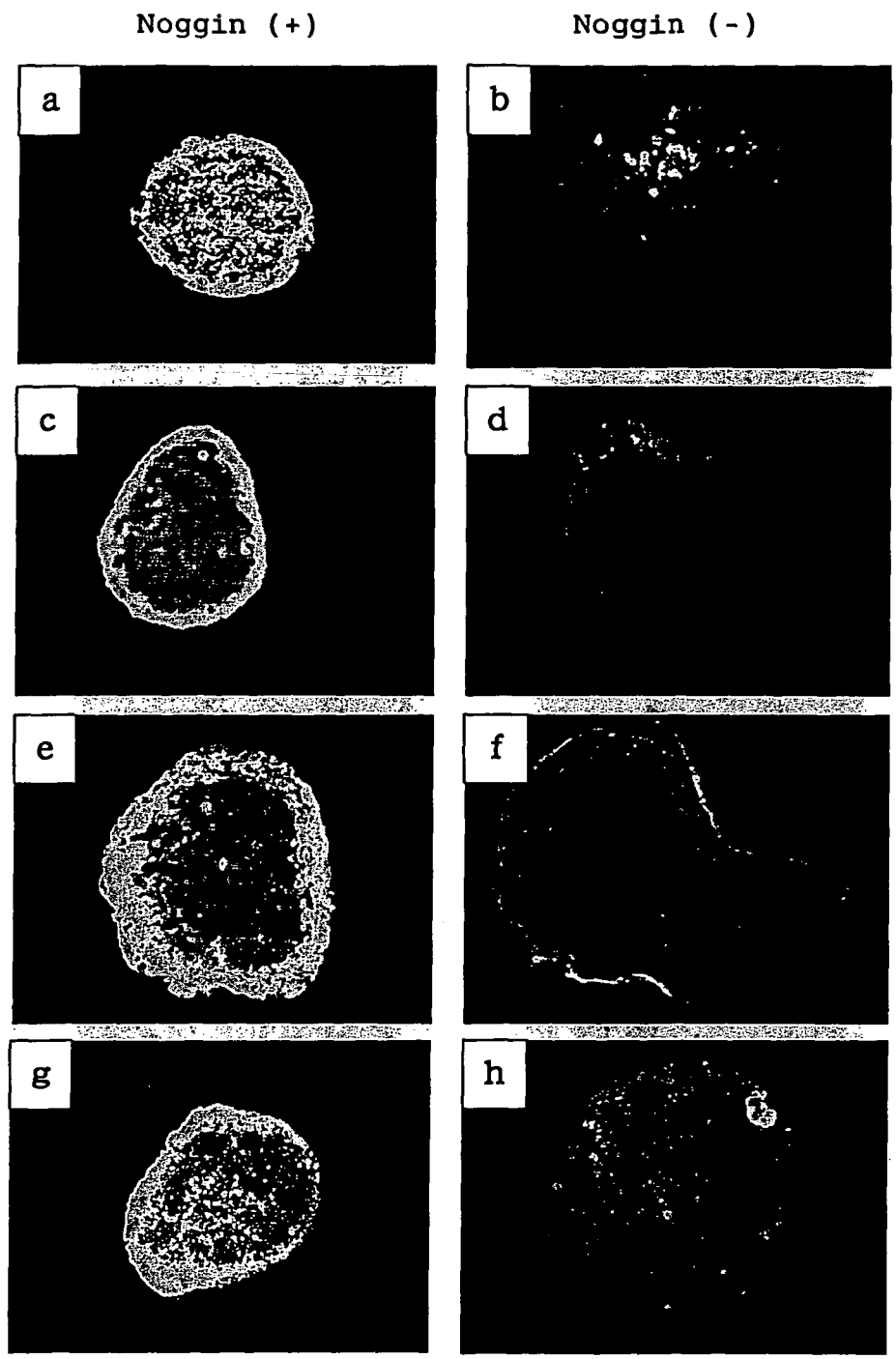
FIG. 5 shows the results of immunocytochemical staining of cardiomyocytes in Noggin (+) and Noggin (−) groups of BBs (derived from EB3 cells) on the $10^{th}$ day of floating culture. a,b: sarcomeric myosin, c,d: troponin I, e,f: α-actinin, g,h: ANP.

The results are shown in FIG. 5. While cells positive for cardiomyocyte-specific marker proteins were observed only in very limited regions of the Noggin (−) group EBs, in the Noggin (+) group EBs myocardial marker-positive cells were found in roughly all the surface layer regions of the EBs. This finding is entirely consistent with the results of observation in Example 1, which showed that while in the Noggin (−) group EBs the beating region was limited to only part of the EBs, in Noggin (+) group EBs beating occurred in almost entire regions of the EBs.

Example 3

Effects of Differences in Noggin Treatment Time and Period on Cardiomyocyte Differentiation from ES Cells To determine the optimum time and period for Noggin treatment, the time of addition of the Noggin protein to the aforementioned floating culture system was varied, and the subsequent effects on myocardial differentiation induction were examined.

The results are shown in Table 1.

TABLE 1

| Pre-differentiation stage Noggin | Differentiation-inducing stage Noggin | Appearance of Beating EBs |
|---|---|---|
| − | − | <10% |
| + | + | 80%< |
| − | + | <20% |
| + | − | <5% |

Table 1 shows the appearance rates of beating EBs (EB3 cell derived) under various culture protocols, indicating the importance of Noggin stimulus before and after EBs formation. In Table 1, "pre-differentiation stage" indicates culture conditions from 3 days before until the start of floating culture, while "differentiation-inducing stage" indicates culture conditions at the point of EBs formation. In Table 1, "+" indicates than Noggin (150 ng/mL) was added to the medium and "−" indicates that it was not added.

First, the necessity of Noggin treatment before and after differentiation was investigated, according to floating culture method. Beating EBs appeared at a high rate when ES cells were cultured in medium containing the Noggin protein (150 ng/mL) for the 3 days before EBs formation and the Noggin protein (150 ng/mL) was then also added at the beginning of floating culture (day 0) as in Examples 1 and 2, but the rate of appearance of beating EBs was much lower when the ES cells were pre-cultured in medium containing no Noggin protein, even when the Noggin protein was then added at the EBs formation. The presence of LIF, which is added to the medium to maintain the ES cells in an undifferentiated state, is also important in the culture of mouse-derived ES cells before floating culture, and when ES cells were cultured without the addition of LIF (2000 U/mL) in pre-differentiation stage, the appearance rate of beating EBs was significantly less even with Noggin treatment.

However, the appearance of beating cardiomyocytes was significantly suppressed when the Noggin protein (150 ng/mL) was also included in the culture after the $5^{th}$ day. Moreover, when it was constantly present for 7 or more days in floating culture there were virtually no beating cardiomyocytes, and induction of differentiation into neuron-like cells was observed as has been reported before (Gratsch & O'Shea, Dev. Biol. 245:83, 2002).

These results show that Noggin treatment is important both before and immediately after the EBs formation in order to efficiently induce differentiation of cardiomyocytes from ES cells, and that the constant presence of a high concentration of the Noggin protein after the induction acts conversely to impede the development of cardiomyocytes.

Example 4

Inhibitory Effects of BMP on the Myocardial Differentiation-Inducing Action of Noggin In order to confirm the possibility that the induction of myocardial differentiation by Noggin treatment on ES cells occurs via the activity of Noggin as a BMP antagonist, we investigated the effects when BMP-2 was added to the medium at the same time as Noggin.

Figure 6:
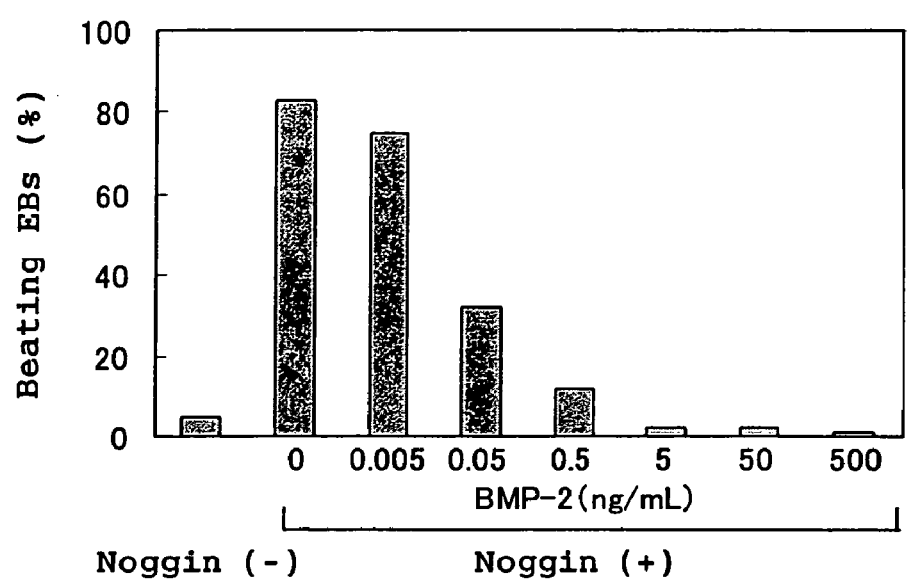
FIG. 6 shows the inhibitory effects of BMP on the effect of Noggin for cardiomyocyte induction.

Floating cultures were performed under the same conditions as in Examples 1 and 2, with various concentrations of BMP-2 included at the same time as the Noggin protein (150 ng/mL) and the effects were investigated with the results shown in FIG. 6. BMP-2 concentration-dependently inhibited the myocardial differentiation-inducing effects of Noggin treatment on the ES cells, and when 5 ng/mL or more of BMP-2 was added virtually no beating EBs appeared.

Example 5

Effects of Noggin Treatment in a Myocardial Differentiation-Induction System Using Feeder Cells It has been reported that cardiomyocyte differentiation can be induced, not using a three-dimensional culture system such as a floating culture or hanging drop culture, by co-culturing ES cells together with ST2 cells, OP9 cells or other stroma cells seeded beforehand on culture plates as supporting cells (feeder cells) (Yamane et al, Methods Mol. Biol. 184:261, 2002; Schroeder et al, Proc. Natl. Acad. Sci. USA 100:4018, 2003). We therefore investigated the effects of Noggin treatment in a differentiation induction system using ST2 cells (purchased from Riken cell bank) as the feeder cells. The ST2 cells were seeded on commercially available 6-well plates for cell culture (Corning), and those cultured to confluence using medium consisting of Dulbecco MEM (Invitrogen) with 10% FBS (Invitrogen) added thereto were used as feeder cells. A suspension of ES cells in a single-cell state was prepared as above, and the feeder was washed twice in PBS and seeded 2000 cells/2 mL medium/well. The appearance of beating cardiomyocytes was then observed microscopically everyday, and after 8 days of culture some of the cells were fixed with 70% ethanol solution, reacted successively with anti-sarcomeric myosin antibodies (MF20; American Type Culture Collection) as the primary antibodies followed by horseradish peroxidase-conjugated secondary antibodies (Histofine Simple Stain PO(M); Nichirei), and finally subjected to a color reaction with ACE (3-amino-9-ethylcarbazole) substrate liquid (Nichirei) and observed under an optical microscope.

Figure 7A:
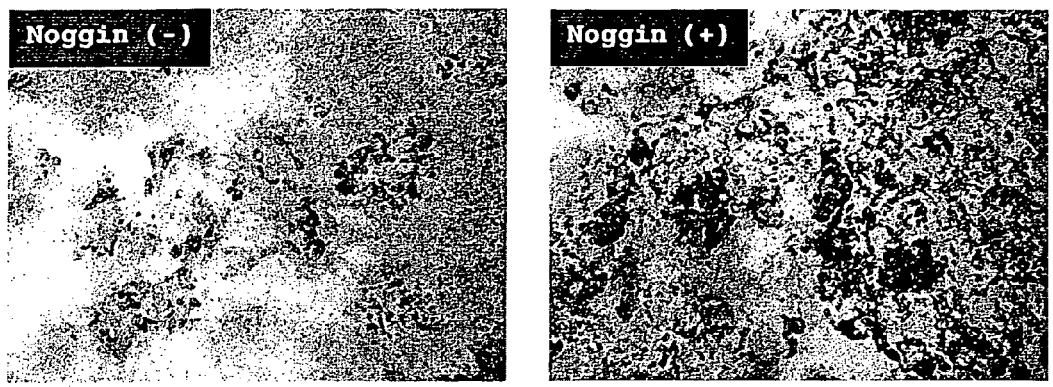
FIG. 7A shows the differentiated cardiomyocytes using co-culture system with feeder cells. ES cells (R1) were seeded on ST2 feeder cells, and myocardial differentiation was investigated by immunocytochemical staining using anti-sarcomeric myosin antibodies (MF20) on the $8^{th}$ day after seeding (n>5). *$p<0.01$ relative to Noggin (−) group.
Figure 7B:
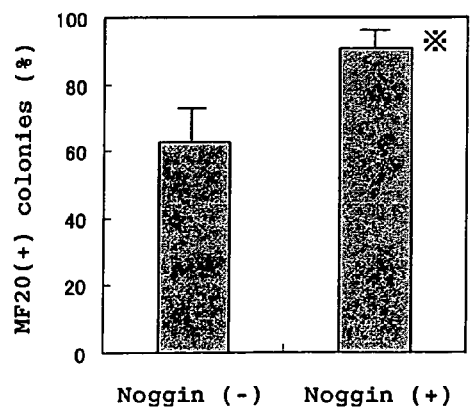
FIG. 7B shows the appearance rate of cardiac colonies from Noggin-treated ES cells using co-culture with feeder cells. ES cells (R1) were seeded on ST2 feeder cells, and myocardial differentiation was judged from the appearance rate of MF20-positive colonies on the $8^{th}$ day after seeding (n>5). *$p<0.01$ relative to Noggin (−) group.
Figure 7C:
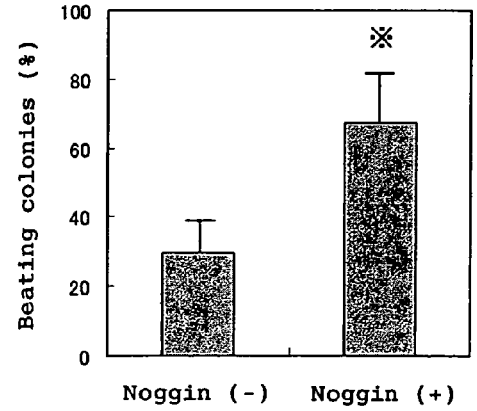
FIG. 7C shows the appearance rate of beating colonies from Noggin-treated ES cells in co-culture with feeder cells. ES cells (R1) were seeded on ST2 feeder cells, and myocardial differentiation was judged from the appearance rate of beating colonies on the $12^{th}$ day after seeding (n>5). *$p<0.01$ relative to Noggin (−) group.

Under these culture conditions, ES cells seeded on ST2 cells formed colonies of a size that could be observed macroscopically within a few days after plating, and cells (colonies) positive for a myocardial cell marker, sarcomeric myosin (hereunder, MF20 positive), were confirmed after 8 days of culture, while beating cardiomyocytes appeared on about the $12^{th}$ day of culture. ES cells which had been cultured in the presence of Noggin protein (150 ng/mL) for the 3 days before plating were seeded on ST2 cells, and cultured in medium containing Noggin (150 ng/mL) for 2 days of co-culture. The results are shown in FIG. 7. While more than 60% of the ES cell-derived colonies formed on the feeder were MF20 positive in the Noggin (−) group, 90% or more of the colonies were positive in the Noggin (+) group, and the percentage of MF20-positive cells in each colony was much higher in the Noggin (+) group than in the Noggin (−) group. Moreover, beating cardiomyocytes appeared at a higher rate in the Noggin (+) group: while about 30% of ES cell-derived colonies formed on feeder cells beat in the Noggin (−) group, about 70% of the colonies were observed to beat in the Noggin (+) group.

Example 6

Effects of Chordin Treatment on Cardiomyocyte Differentiation from ES Cells

Figure 8:
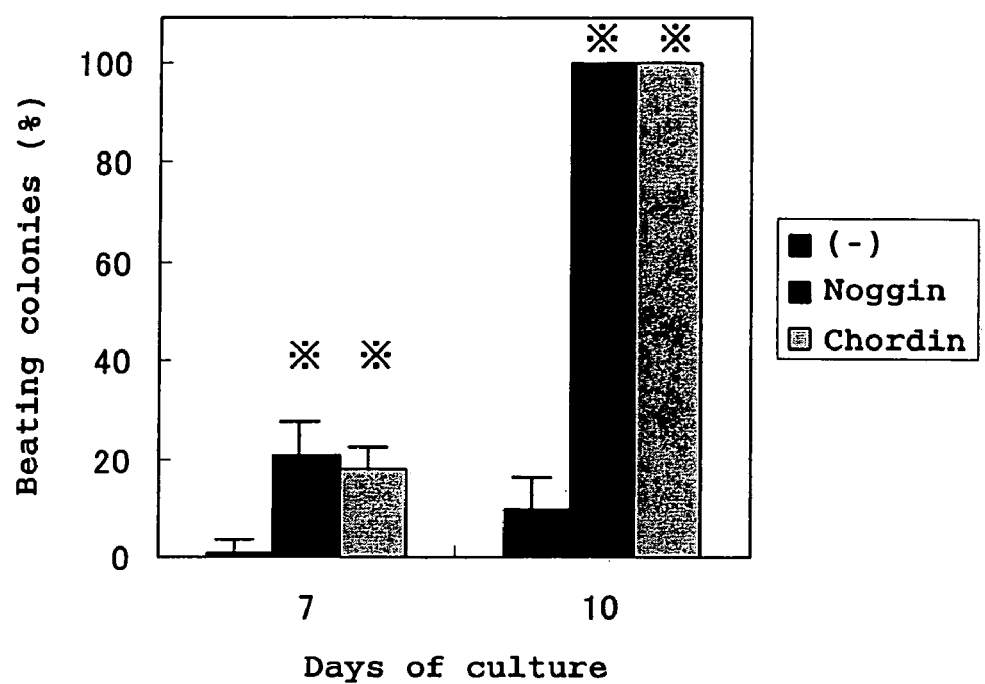
FIG. 8 shows the effects of addition of the Chordin protein (500 ng/mL) on the appearance rate of beating EBs, compared to those of Noggin protein (500 ng/mL) addition, using hanging drop method. Days of culture means days from the beginning of hanging drop culture (n 8). *$p<0.01$ relative to untreated group (−).

The myocardial induction effects of Chordin, which like Noggin is known to act as a BMP antagonist, were studied and compared with those of Noggin. A commercially available recombinant Chordin-Fc chimera protein (Recombinant Mouse Chordin/Fc Chimera, R & D Systems: hereunder called just "Chordin (protein)" was used as the Chordin protein. A hanging drop culture was performed by the same methods as in Example 1 using ES cells which had been cultured for 3 days in medium to which Noggin (500 ng/mL) or Chordin (500 ng/mL) had been added or medium to which neither factor had been added. On the 4$^{th}$ day of hanging drop culture, EBs were collected and seeded on cell culture dishes, and differentiation into cardiomyocytes was then further induced by adhesion culture. As a result, beating cardiomyocytes appeared in the Chordin-treated ES cells at about the same rate as in the Noggin-treated ES cells (FIG. 8), confirming that like Noggin, Chordin has a myocardial differentiation-inducing effect on ES cells.

The effects of Chordin were also studied using a different EBs formation/myocardial differentiation induction method. ES cells which had been cultured for 3 days in medium to which Noggin (150 ng/mL) or Chordin (150 ng/mL) had been added or medium to which neither factor had been added were seeded on commercially available spheroid culture plates (96-well multi-plates, Sumitomo Bakelite) to form EBs and induce differentiation of cardiomyocytes. In this case, a group with added Chordin (150 ng/mL) and a group without added Chordin were established.

Figure 9:
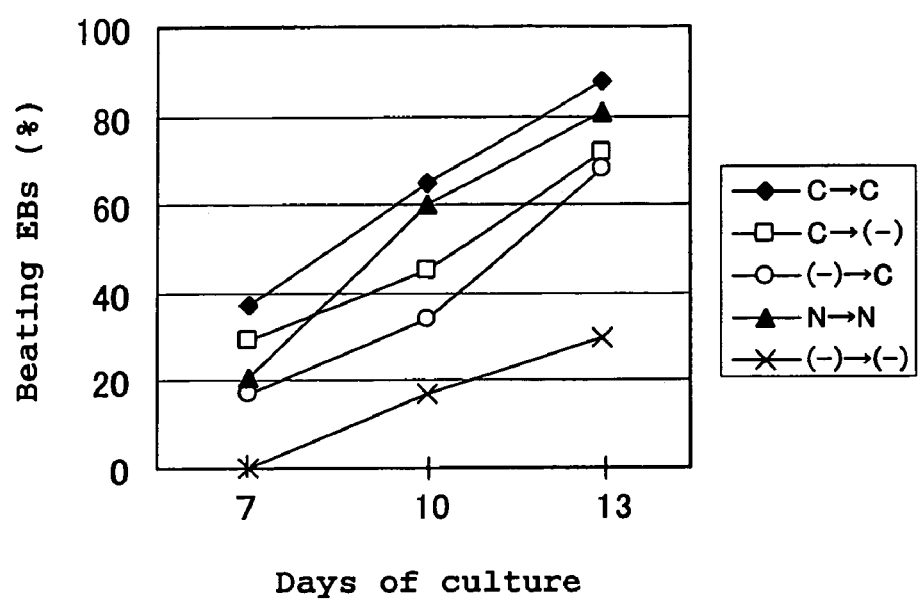
FIG. 9 shows the effects of addition of the Chordin protein (150 ng/mL) on appearance rate of beating EBs from ES cells (R1) using floating culture plate. C: Chordin, N: Noggin (150 ng/mL), (−): untreated. "A"→"B" means as followed; A and B as treated protein before and after EBs formation, respectively.

As shown in FIG. 9, beating cardiomyocytes were evident in the Chordin-treated ES cells (C→C in figure) as they were in the Noggin-treated ES cells (N→N in figure), confirming again that Chordin has the same myocardial differentiation induction effect as Noggin in ES cells. The myocardial differentiation promotion effect was also significantly higher in the group that Chordin was pre-treated during 3 days before induction and not treated after EBs formation (C→(−) in figure), and in the group that was not treated with Chordin before EBs formation but to which Chordin was added after EBs formation ((−)→C in figure) than in the untreated group ((−)→(−) in figure). The same effect was also seen when Noggin was used in place of Chordin, with a much stronger myocardial differentiation promotion effect being confirmed in the group that was treated with Noggin for 3 days before EBs formation but to which no Noggin was added after EBs formation and in the group that was not treated with Noggin before EBs formation but to which Noggin was added after EBs formation than in the untreated group.

Next, embryonal carcinoma cells (hereunder called EC cells), which are similar to ES cells, were used to investigate the effectiveness of Noggin and Chordin treatment in human cells. NCCIT cells (purchased from American Type Culture Collection), a human EC cell line, were cultured for 3 days in the same way as the aforementioned mouse ES cells in medium to which Noggin (15 ng/mL) or Chordin (15 mg/mL) had been added or medium to which no factor had been added. These were then seeded on commercially available floating culture plates to form EBs which were cultured for 14 days. Gene expression or protein production of cardiomyocyte-specific markers was then investigated by PCR or immunocytochemical staining using the same methods as in Example 2. As a result, induction of expression/production of the myocardial marker myosin was confirmed in NCCIT cells treated with Noggin or Chordin.

Example 7

Effects of Other BMP Antagonists on Cardiomyocyte Differentiation from ES Cells

Next, the effects of the 4 BMP antagonists Follistatin, DAN, Caronte (chicken Cerberus-like factor) and gremlin were investigated (Fc chimera-type recombinant proteins; R&D Systems). ES cells which had been cultured for 3 days in medium to which the aforementioned BMP antagonists (150 ng/mL) had been added and medium to which no BMP antagonist had been added were seeded on commercially available floating culture plates (96-well multiplates; Sumitomo Bakelite) to form EBs and induce differentiation into cardiomyocytes.

Figure 10:
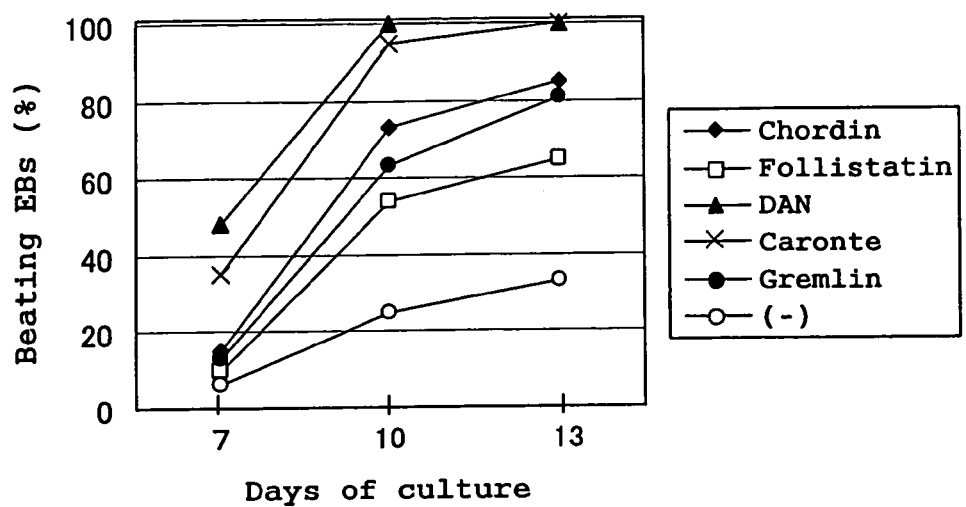
FIG. 10 shows the effects of addition of various BMP antagonist proteins (150 ng/mL each) on appearance rate of beating EBs from ES cells (R1) using floating culture plate.

As a result, myocardial differentiation induction with these various factors was the same or greater as that obtained with Noggin and Chordin (FIG. 10). Moreover, similar effects were also obtained from addition of a recombinant protein (Recombinant Mouse BMPR-1A/Fc Chimera; R & D Systems) which corresponds to the extracellular domain of BMP receptor 1A and competitively inhibits binding of BMP family molecules with endogenous receptors.

The invention claimed is:

1. A method for inducing differentiation of cardiomyocytes from mammalian pluripotent stem cells, comprising
   (1) culturing mammalian pluripotent stem cells in a culture medium including a substance that inhibits BMP signaling within three days before inducing differentiation and/or within the first three days of the differentiation-inducing stage; and
   (2) obtaining cardiomyocytes.

2. The method according to claim 1, wherein the step of culturing stem cells comprises a step of forming embryoid bodies by floating aggregation culture.

3. The method according to claim 1, wherein the step of culturing stem cells comprises a step of co-culturing with feeder cells.

4. The method according to claim 1, wherein the step of culturing stem cells comprises a step of plate culturing on a culture container.

5. The method according to claim 1, wherein said culturing occurs within the first three days of the differentiation-inducing stage.

6. The method according to claim 1, wherein said culturing occurs within three days before inducing differentiation.

7. The method according to claim 1, wherein said culturing occurs within three days before inducing differentiation, and within the first three days of the differentiation-inducing stage.

8. The method according to claim 1, wherein the substance that inhibits BMP signaling is a BMP antagonist.

9. The method according to claim 8, wherein the BMP antagonist is one or more selected from a group comprising Noggin, Chordin, fetuin, follistatin, sclerostin, DAN, Cerberus, gremlin, Dante and related proteins thereof.

10. The method according to claim 1, wherein the pluripotent stem cells are embryonic stem cells, cells with a similar morphology to embryonic stem cells, embryonic germ cells, or multipotent adult progenitor cells.

11. The method according to claim 1, wherein the pluripotent stem cells are embryonic stem cells.

12. The method according to claim 1, wherein said culturing occurs within three days before inducing differentiation, and at the beginning of the differentiation-inducing stage.

13. A method for inducing differentiation of cardiomyocytes from mammalian pluripotent stem cells, comprising
   (1) culturing mammalian pluripotent stem cells in a culture medium including a substance that inhibits BMP signaling within three days before the formation of embryoid bodies and/or within the first three days after the formation of embryoid bodies; and
   (2) obtaining cardiomyocytes.

14. The method according to claim 13, wherein said culturing occurs within three days before the formation of embryoid bodies.

15. The method according to claim 13, wherein said culturing occurs within the first three days after the formation of embryoid bodies.

16. The method according to claim 13, wherein said culturing occurs within three days before the formation of embryoid bodies and within the first three days after the formation of embryoid bodies.

17. The method according to claim 16, wherein said culturing occurs within three days before the formation of embryoid bodies and immediately after the formation of embryoid bodies.

* * * * *